(12) United States Patent
Schmitt et al.

(10) Patent No.: US 8,229,197 B2
(45) Date of Patent: Jul. 24, 2012

(54) METHOD FOR PLANNING AN ANGIOGRAPHIC MEASUREMENT

(75) Inventors: Peter Schmitt, Weisendorf (DE); Katrin Christel Sprung, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1051 days.

(21) Appl. No.: 12/037,209

(22) Filed: Feb. 26, 2008

(65) Prior Publication Data

US 2008/0205725 A1    Aug. 28, 2008

(30) Foreign Application Priority Data

Feb. 26, 2007  (DE) .......................... 10 2007 009 185

(51) Int. Cl.
*A61B 5/055* (2006.01)
*G06K 9/00* (2006.01)
(52) U.S. Cl. ......... 382/130; 600/410; 600/414; 600/419
(58) Field of Classification Search .................. 382/128, 382/130–131; 600/410, 414, 416, 419; 324/306
See application file for complete search history.

(56) References Cited

U.S. PATENT DOCUMENTS

| | | | |
|---|---|---|---|
| 5,928,148 A * | 7/1999 | Wang et al. .................. | 600/420 |
| 6,195,409 B1 | 2/2001 | Chang et al. | |
| 6,408,201 B1 | 6/2002 | Foo et al. | |
| 7,312,810 B2 | 12/2007 | Hayashi et al. | |
| 2002/0091316 A1 * | 7/2002 | Foo et al. ........................ | 600/420 |
| 2004/0008028 A1 | 1/2004 | Horger et al. | |
| 2005/0264286 A1 * | 12/2005 | Harder .......................... | 324/307 |
| 2006/0178836 A1 * | 8/2006 | Bai et al. ........................ | 702/19 |
| 2008/0253634 A1 * | 10/2008 | Hay et al. ....................... | 382/130 |

* cited by examiner

*Primary Examiner* — Jack Berman
*Assistant Examiner* — David E Smith
(74) *Attorney, Agent, or Firm* — Schiff Hardin LLP

(57) ABSTRACT

In a method for planning of an angiography measurement of a body region in a magnetic resonance system, the body region being larger than the maximum field of view of the magnetic resonance system, and wherein the MR system has a control unit for controlling the workflow of the angiographic measurement, an upper boundary and a lower boundary of the body region are established. The control unit divides the body region into sub-measurement regions and sub-measurements dependent on the established boundaries. The sub-measurement regions and sub-measurements are measured in succession. The arrival of an injected test bolus of a contrast agent into the various sub-measurement regions is detected using MR measurements. The transit time of the test bolus through the body region for the angiographic measurement is determined, and the control unit also determines the workflow of the angiography measurement, including determining the sequence of the measurements of the sub-measurement regions and the time duration of the individual sub-measurements for the sub-measurement regions.

13 Claims, 6 Drawing Sheets

| Sub-measurement | Measurement parameters | Residence duration of contrast agent | Alternative measurement parameters | ok | Change |
|---|---|---|---|---|---|
| | Wait time before 1st measurement | | | | |
| 1 | Acquisition time 18 s<br>Number of slices 56<br>Resolution | 15s | Acquisition time 15 s<br>Number of slices 52<br>Resolution | ☐ | ☐ |
| | Table feed | | | | |
| 2 | Table feed | | | | |
| 3 | | | | | |

51 / 52 / 53 / 54

METHOD FOR PLANNING AN ANGIOGRAPHIC MEASUREMENT

BACKGROUND OF THE INVENTION

1. Field of the Invention

The present invention concerns a method for planning an angiographic (image acquisition) measurement of a body region in a magnetic resonance system (MR system) as well as the MR system for this.

2. Description of the Prior Art

As has long been known, in MR imaging, is sensitive to the movement of the nuclear spins that generate the MR signal. These effects can be used for acquisition of angiographic images, i.e. images of the vessels of the examined person. Angiographic techniques are known that are based only on the flow effects of the spins located in the body. Furthermore, it is possible to improve such angiography acquisitions with the aid of contrast agents. Given use of a contrast agent, for the angiographic representation of vessels over a larger anatomical region in the body it is difficult to track the contrast agent introduced into the vascular system in real time given passage (flow) through the examined region.

It is hereby important to temporally match the procedures for all acquisitions to one another in order to optimally depict the vessels in each body region. In angiography acquisitions these are also matched to each patient since the individual circulation time of each patient changes the passage speed of the contrast agent. When very large vessel segments (such as, for example, the entire vascular tree in the body) is to be depicted, this often cannot be accomplished with a single contrast agent injection. This particularly applies when the contrast agent flows relatively quickly through the body.

The apparatus operator is thereby required to individually adapt the measurement parameters for the imaging, but this results in many possible sources of error. For example, that the image quality is degraded by the adaptation of the acquisition parameters (such as the shortening of the acquisition duration) in order to be able to track the contrast agent course. Experientially, combining all of the measurement parameters dependent on one another such that a good image quality is always achieved causes problems for the users of MR systems. The temporal sequence of the acquisition is often incorrect, such that it can occur that the images display not only the arterial image information that is important for the diagnosis finding, but also display signal contributions of the venous (return) flow of the contrast agent. It is likewise possible that the image quality is not sufficient to allow the diagnosis when the parameters of the spatial resolution vary too severely for different measurement regions.

Overall this acquisition technique requires a great deal of knowledge on the part of the operator, so the image quality depends very strongly on the experience of the person who implements the angiographic measurement.

SUMMARY OF THE INVENTION

An object of the present invention is to provide a method for planning an angiography measurement in which angiography exposures can be generated with good image quality independent of the experience of the operator.

This object is achieved according to the invention, by a method for planning an the angiography measurement wherein a body region is angiographically presented that is larger than the maximum field of view of the magnetic resonance system. The magnetic resonance system has a control unit for controlling the workflow of the measurement. The inventive method includes the step of establishing an upper boundary and a lower boundary of the body region in which the angiography measurement should be executed. Dependent on the established boundaries, the control unit now divides the body region into sub-measurement regions and sub-measurements that are measured in succession. In a further step the arrival of an injected test bolus of a contrast agent into the various sub-measurement regions is detected using MR measurements, from which the transit time of the test bolus through the body region can be determined. The control unit can now determine the workflow of the angiography measurement dependent on the determined transit time. The sequence of the measurements of the sub-regions and the time duration of the individual sub-measurements for the sub-measurement regions are established in a further step. According to the invention, assistance in the measurement planning is provided by the MR system (in particular by the control unit), which ensures that the sub-measurement regions are correctly selected and that the measurement times of the sub-measurements in the sub-measurement regions are set such that the bolus course of the contrast agent is detected in the different sub-measurement regions. In the present context the term "transit time" means the arrival of the contrast agent in various body regions. The term "transit time" consequently encompasses a number of times and represents the contrast agent course. It is not necessary to determine the arrival of the test bolus in all sub-measurement regions. It is also possible to detect this only in some sub-measurement regions and to determine the contrast agent course in the body from this. For example, for angiography of the pelvic and leg region, the test bolus can be detected only in the abdomen and in the lower leg even though three sub-measurement regions abdomen, thigh and lower leg were defined.

Furthermore, it is possible for overview measurements for planning of the angiography measurement to be implemented, wherein the upper boundary and lower boundary of the body region for the angiographic measurements are established. For whole-body angiography it is possible for the control unit to automatically find the upper boundary and the lower boundary of the MR measurement, for example by detecting the upper end of the head and the lower end of the feet. For partial-body angiographies, an operator of the magnetic resonance system can also establish the upper and lower measurement boundaries on the overview images. Naturally it is also possible for the operator to establish only one measurement boundary while the other measurement boundary is established automatically by the upper end or lower end of the examined person.

When the body region to be measured is now known with the upper boundary and the lower boundary, the control unit can determine the number of the sub-measurement regions and the overlap of the sub-measurement regions that is necessary in order to cover the body region to be imaged. Furthermore, the sub-measurements accruing in the sub-measurement regions can be established with the associated sequence parameters such as acquisition time, slice thickness etc. An overlapping of the sub-measurement regions is useful in order to be able to later merge the calculated angiography images into a total image without error. Furthermore, it is possible for the operator to receive the result presented as a measurement protocol, with the individual measurements being additionally graphically displayed in the overview images. The operator here has the possibility to effect individual adaptations. All variables (such as division into sub-measurement regions or sequence parameters) proposed by the control unit are advantageously displayed to the operator, who can alter these if desired.

Furthermore, it is possible for the control unit to establish the position and time duration of test measurements with which the course of the test bolus through the test measurement regions can be tracked after an injection. The test bolus is advantageously anatomically administered such that the contrast agent flow through the body region to be imaged can be detected. The MR system can make an automatic suggestion which the user can alter or accept. The position and time duration of the test measurements are hereby established in agreement with the determined sub-measurement regions, wherein the established position is displayed again to the operator. The operator can either accept the position or effect changes. Furthermore, after the contrast agent injection of the test bolus the arrival of the test bolus can be detected by detecting when the contrast in the vessel reaches a threshold. If the system has detected the arrival of the test bolus, it can automatically transition to the next test measurement, such as by the table on which the examination person lies being automatically shifted, for example. At the end of all test measurements it is possible to determine the transit time of the test bolus through the body region in which angiographic exposures should be made.

If the transit time of the test bolus is now known, with this information it can be checked whether the sub-measurement regions established at the beginning and the associated sub-measurements can be implemented. The time duration for the necessary table feed (that is necessary to move the examination person from one sub-measurement region to the next sub-measurement region at different table positions) can be taken into account.

In a further embodiment, the sub-measurement regions calculated by the control unit and the workflow diagram for the angiographic measurement are presented on the overview images, and the operator can modify or adopt the position of the sub-measurement regions and the sub-measurement regions and the workflow diagram. The time curve of the contrast agent can likewise be graphically presented in the overview images and the times that are required in order to reach a specific test measurement region after the injection can be shown.

When the transit time of the test bolus is known, the maximum acquisition duration for each sub-measurement region can be determined, wherein the table feed that can be required between the measurements of sub-measurement regions should hereby be taken into account. If this acquisition duration is known, the optimal image measurement parameters in order to optimize the image quality overall can be determined for each sub-measurement region. When the determined acquisition durations of a number of sub-measurement regions are longer than the time data that result from the time curve of the test bolus, it can be necessary to proceed to a double injection scheme. This means that the various sub-measurement regions cannot be measured with a single contrast agent injection bur rather that two contrast agent injections are necessary in total.

In order to be able to establish a common start point for the beginning of the measurement series and the contrast agent injection, it is possible to introduce a time offset before the measurement of the first sub-measurement region so that the angiographic measurement and the injection of the contrast agent can be started simultaneously and nevertheless the contrast agent arrives in the first sub-measurement region and is detected upon measurement of said first sub-measurement region.

The above object also is achieved in accordance with the invention by a magnetic resonance system for planning and implementation of an angiographic measurement, wherein a control unit is provided that divides the body region (established from the upper boundary and lower boundary of the body region) into sub-regions with sub-measurements, dependent on the boundaries. A detection unit detects the arrival of the injected test bolus of the contrast agent in the various sub-measurement regions. A computer determines the transit time of the test bolus through the body region for the angiography measurement. The control unit determines the workflow of the angiographic measurement and in particular determines the sub-measurement regions and the time duration of the individual sub-measurements for the sub-measurement regions. Since the parameters that are difficult for the operator to determine are determined automatically after the injection of the test bolus, it is also possible for an untrained operator to acquire angiography exposures over larger measurement regions with good signal quality.

DESCRIPTION OF THE PREFERRED EMBODIMENTS

Figure 1:
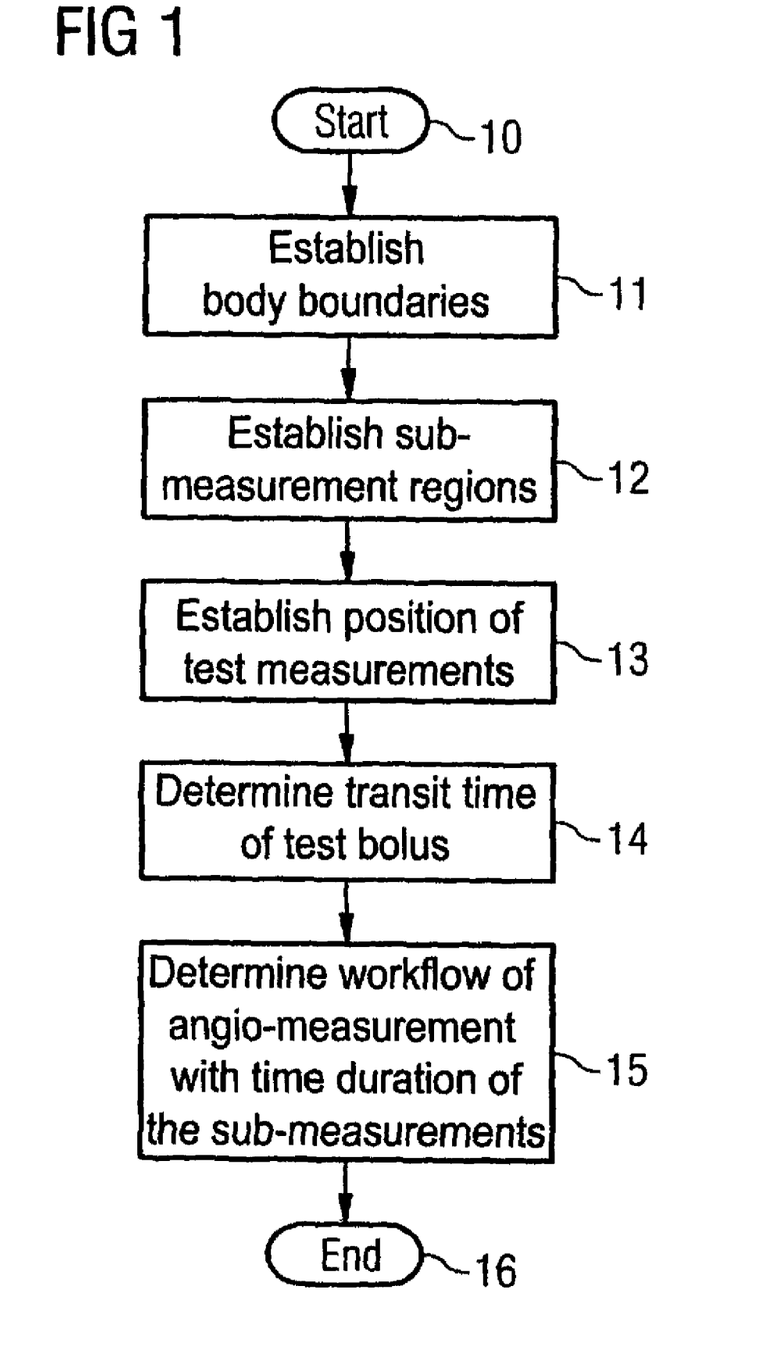
FIG. 1 is a flowchart of an embodiment for planning of an angiography measurement according to the invention.

A flowchart diagram that shows the basic steps for planning of an angiography measurement is shown in FIG. 1. The flowchart shown in FIG. 1 starts with step 10. In a next step the start and end points of the measurements (i.e. the upper boundary and lower boundary of the angiography measurements) are now established (step 11). In the event that it is a whole-body measurement, the start point and end point of the measurement (namely the upper end at the head and the lower end at the feet of the examined person) can be found automatically. In the case of an angiographic measurement that does not concern the entire body of the examination person, it is possible that the operator establishes the upper boundary and lower boundary manually.

If the measurement region to be covered is now known, this can be divided automatically into sub-measurement regions (step 12) by a control unit of the MR system. This division of the examination region into sub-measurement regions in particular depends on the size of the field of view that the MR system can cover in the longitudinal direction of the examination person at a predetermined table position. Furthermore, the sub-measurement regions are established such that there is an overlap of the different regions. It is thereby possible to merge images generated from the shown anatomical into a sum image without errors. The various positions of the test measurements in which the contrast agent flow through the examined region can be detected with the aid of a contrast agent test bolus are now established in a next step 13. This test bolus can be a small quantity of a contrast agent typically used in MR angiography acquisitions. This test bolus is now conveyed through the vascular system, with the contrast agent normally influences parameters such as the T1 time and T2 time or the T2* time. The arrival of the contrast agent bolus can typically be detected via a signal change in the vessel. The transit time of the test bolus through the examined acquisition region can now be established from the contrast agent course in step 14. If the transit time of the test bolus is now known, the workflow of the angiography measurement can be determined with the time duration and position of the sub-measurements (step 15). In the event that the MR system is a system in which the examination person is examined on a stationary table after a table feed, the sub-measurement regions correspond to the measurement regions at a specific table position. However, the invention is also applicable at MR systems in which the signal detection ensues while the table with the examination person is moved through the MR system. Due to the continuous table feed, here the measurement regions are not limited to the regions in which the table stands still. However, it can be assumed from this that the entire region to be presented is divided up into sub-measurement regions. Given a continuous table feed the feed speed of the table during the measurement can be adapted using the determined transit time of the test bolus. Given a continuous table feed the time characteristic of the arrival of the bolus flow can also be used, for example for the optimization of the table speed along the table movement direction and/or the regulation of the table movement characteristic over the duration of the measurement time (for example adaptation of the table speed in the individual body regions).

Figures 2, 2A:
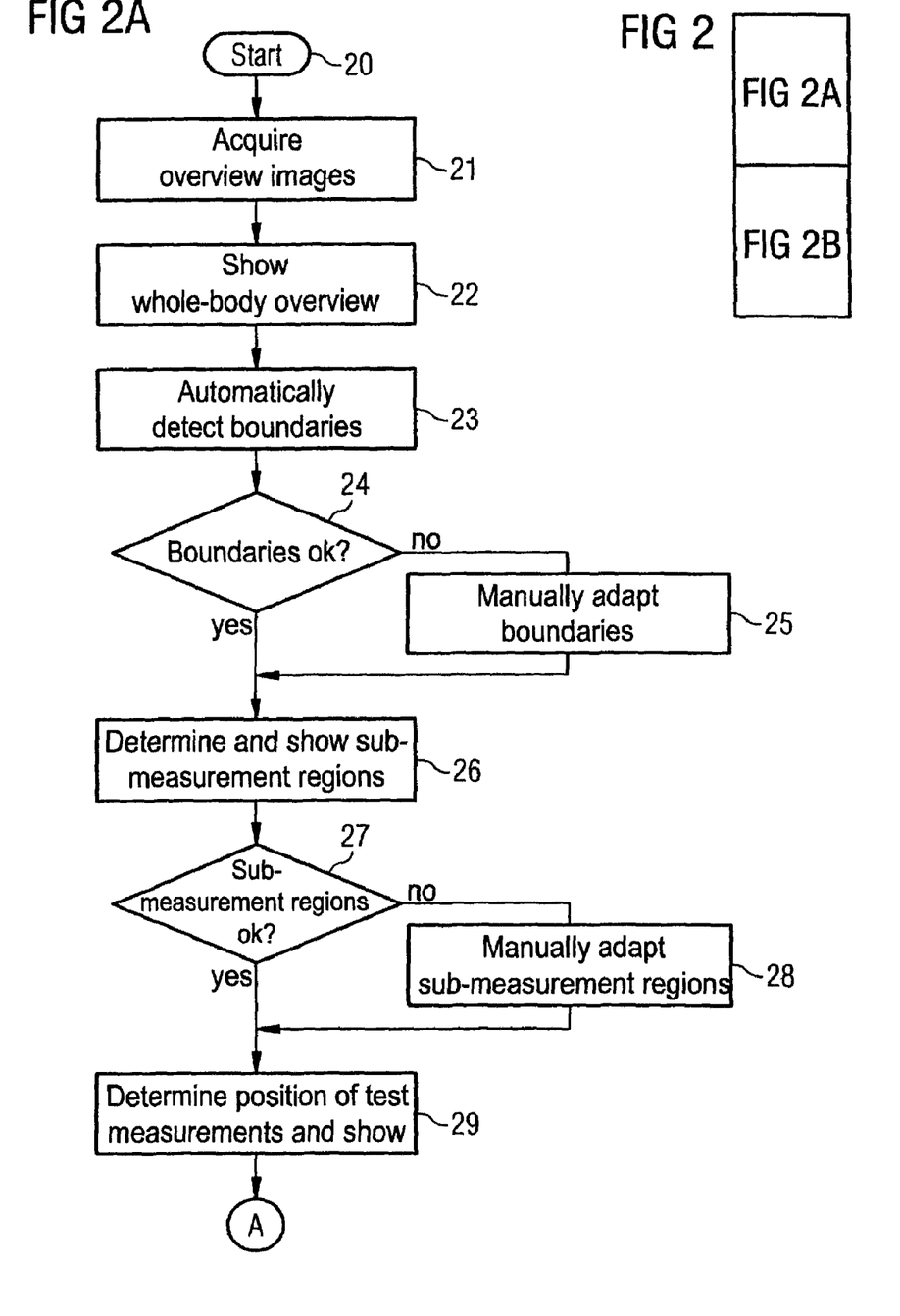
FIG. 2 shows the combining of FIGS. 2A and 2B.
FIGS. 2A and 2B show a flowchart of a further embodiment for planning of an angiography measurement according to the invention.
Figure 2B:
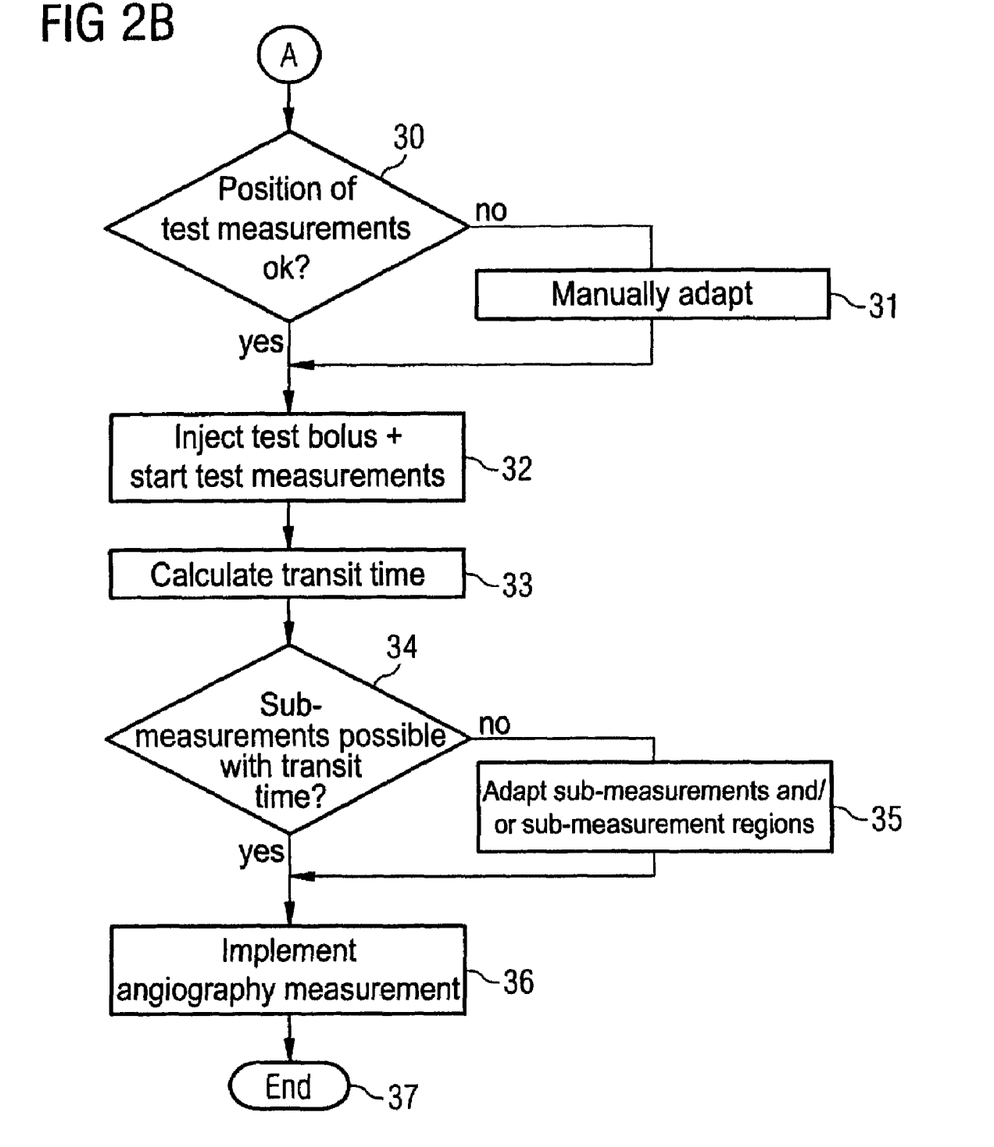
Figure 3:
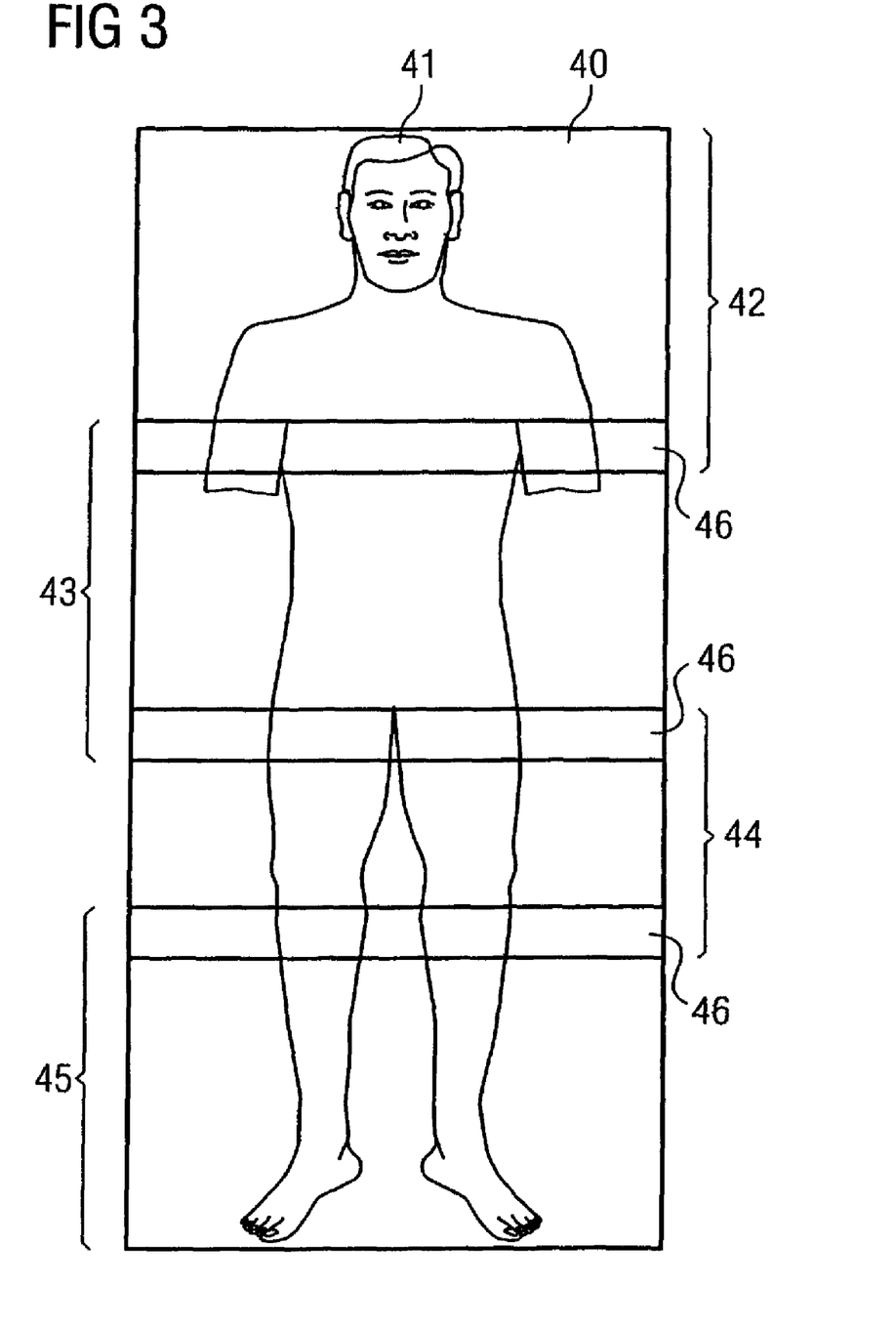
FIG. 3 shows an overview image with the automatically determined sub-measurement regions.
Figure 4:
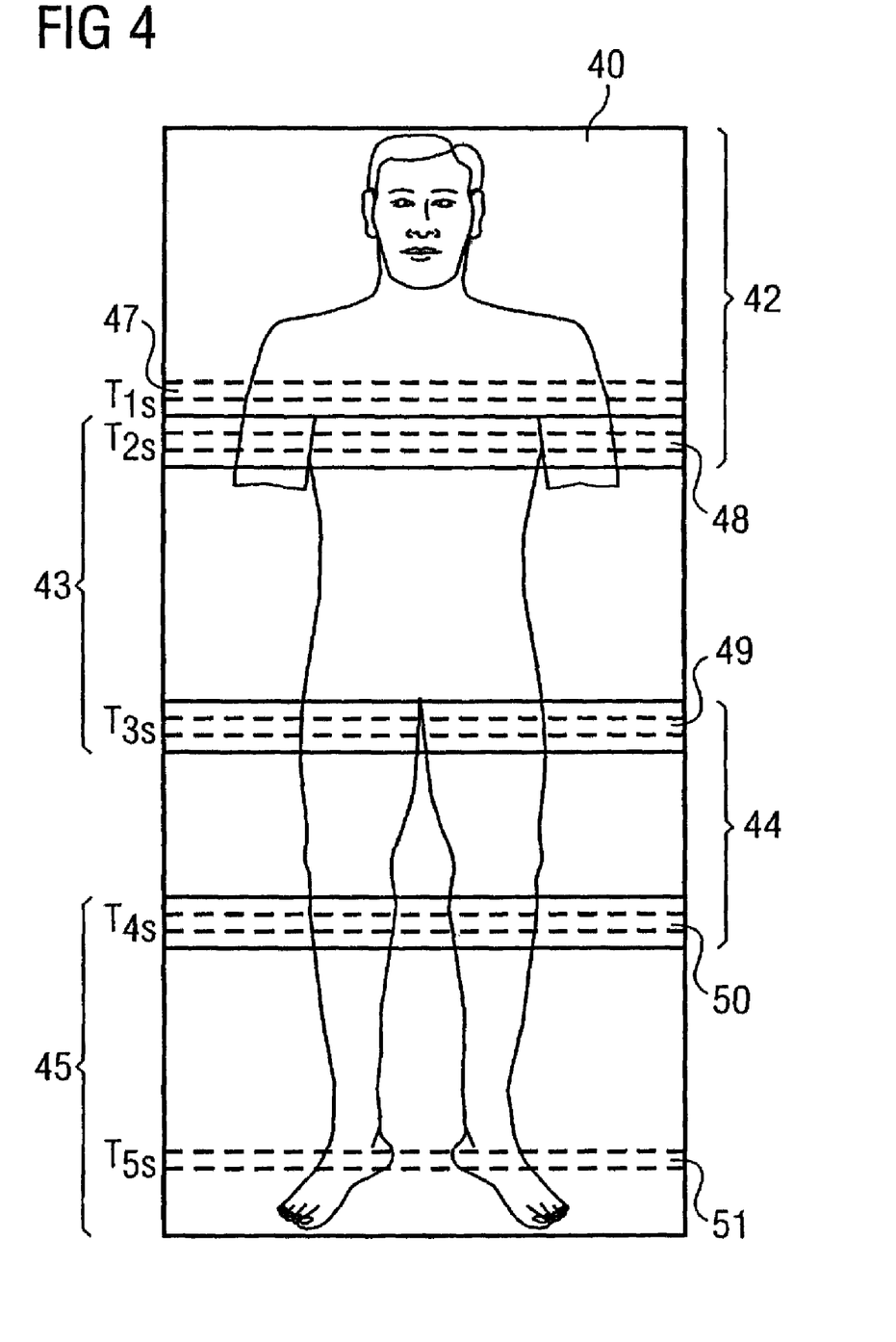
FIG. 4 shows the overview image of FIG. 3 with the position of the test measurement regions and the calculated transit time for the contrast agent.

A more detailed form of the planning of an angiography measurement according to the invention is shown in FIG. 2. The steps presented in FIGS. 2a and 2b are likewise explained in connection with FIGS. 3 through 5. The shown exemplary embodiment is the planning of a whole-body angiography, wherein the presented method can likewise be applied given a partial body angiography. The method starts in step 20. In a step 21 overview images are acquired as they are presented, for example, in FIGS. 3 and 4. Given whole-body measurements coronal slice blocks can be used to show the vessels. In order to be able to plan these, overview exposures of all slice planes of every body region are produced beforehand in order to be able to plan the high-resolution vessel images. These overview measurements can be acquired with predetermined imaging parameters, whereby the individual partial overview exposures are combined. A composite overview exposure 40 results as shown in FIGS. 3 and 4. In the shown overview exposure 40 the coils for detection of the MR signal are arranged such that the entire body can be imaged up to the arms of the examined person (step 22). Given a whole-body measurement it is possible to automatically establish the upper and lower measurement boundaries for each subsequent angiographic measurement (step 23). If it is not a whole-body measurement, the upper and lower measurement boundaries are determined manually in step 23. For example, the operator can establish points on the overview image and defined these as the upper boundary and lower bound. In all other steps the partially body measurement coincides with the workflow for the whole-body measurement presented in FIGS. 2A and 2B.

The detected boundaries are checked by the operator in step 24, wherein said operator can either confirm the measurement boundaries or manually adapt them in step 25 in the event that this is necessary. The system can subsequently automatically proceed with step 26, in which the control unit of the MR system suggests the position of the sub-measurements dependent on the measurement boundaries. Predetermined parameters from predetermined protocol structures can again be used as the base data for these. These sub-regions can be shown on the overview image, as is to be seen in FIG. 3. In the shown embodiment the examined body 41 is divided into a first sub-measurement region 42 from the head to the chest. Furthermore, a second sub-measurement region from below the arms to below the torso is provided (sub-measurement region 43). Sub-measurement regions 44 and 45 are provided at the feed. As is to be recognized from FIGS. 3 and 4, successive measurement regions respectively overlap in an overlap region 46. Among other things, how large the maximum depiction capability of the MR system is in the z-direction (i.e. in the longitudinal direction of the examination person) can be taken into account in the determination of the boundaries of the sub-measurement regions. A minimal overlap is maintained for the composition of the individual measurements. Finally, the number of the sub-measurement regions (which can be different depending on the size of the examination person) results from the size of the examination person and the presentable field of view.

As shown in FIG. 2A, in step 27 it is now queried whether the selection of the sub-measurement regions is satisfactory for the operator. The operator now has the possibility to accept or manually adapt the selection (step 28). The operator can subsequently confirm the selection and the workflow automatically proceeds with the next step (which is identified with step 29). In step 29 the position of the test measurements can now be determined, wherein for example the position of the test measurements can be selected using the previously determined sub-measurement regions. The positions of the proposed test measurements are to be recognized in dashed representation in FIG. 4. In the shown embodiment these test measurements are transversal measurements in order to be able to detect the passage of a test bolus. As shown in FIG. 4, a first transversal orientation 47 is proposed as a position, whereby in the shown exemplary embodiment the position lies in the lower quarter of the first sub-measurement region 42. In the remaining sub-measurement regions the position of the test region is suggested at the upper edge of the sub-measurement, as is to be recognized in the shown test measurement regions 48-51. As can be seen FIG. 2B, the query to accept the position of the test measurements or to manually adapt these (step 31) in turn ensues in step 30. In order to check whether the test bolus is correctly positioned, the operating personnel can click on the slice of the measurement and automatically receives the display of the anatomically closest slice, wherein these can be slices that, for example, have occurred in the overview measurements. If no satisfactory slice should be present, the operator can decide whether she would like to check the position via a measurement of the slice without contrast agent. If all slices are checked, the operator confirms the position of the test measurements and the system automatically proceeds in the next step. In a next step 32 a small quantity of contrast agent is injected as a test bolus into the examination person, wherein the test measurement workflow can be started simultaneously. The table is hereby positioned beforehand in the magnetic resonance system so that the test measurement is begun with the measurement in the first position. By post-processing of the generated MR images from the test measurements (for example via subtraction of the individual images) it can now be detected when the contrast agent reaches the shown slice. For example, if the system detects that the injected contrast agent test bolus has reached the slice 47, the system automatically proceeds to the anatomically nearest test measurement (the slice 48 in the shown exemplary embodiment). After all positions of the test measurements have been run through, the transit time of the test bolus through the body of the patient can be calculated in a step 33. In a step 34 it can now be checked whether the measurements are possible with the calculated transit time as was determined at the start in step 26. The maximum acquisition duration of each individual measurement region can be established using the time information from each sub-measurement region. The duration for the table feed should be considered.

The optimization of the measurement parameters can now ensue with the aid of the measurement parameters that were determined in step 26. The following scenarios are hereby possible. The determined maximum duration of the sub-measurement regions corresponds to the time duration based on the basic parameter set, such that no adaptation is necessary. The determined acquisition duration of a sub-measurement region is shorter than the time duration based on a basic parameter set. In this case the parameters must be adapted such that the acquisition time is shortened in total so that the contrast agent course can be tracked. In the event that the determined acquisition duration of the sub-measurement regions is longer than the time duration that was calculated with the base parameter set, the parameters can be adapted such that the acquisition time is extended in total. When the acquisition duration of a plurality of sub-measurement regions is shorter than the time duration that was proposed in step 26 based on a basic parameter set, it is possibly necessary to switch over to a method in which the vessels are shown not with one contrast agent injection but rather with two or more contrast agent injections. In the event that an adaptation is necessary, this ensues in step 35. The planned angiography measurement in step 36 can subsequently be implemented before the method ends in step 37. Acquisitions with and without contrast agent are hereby compared with one another, wherein the difference signal represents the vessel course.

The transit times determined via the test bolus are shown in FIG. 4. The test bolus reaches the first test position at a point in time T1, the test position 48 at a point in time T2, the test position 49 at a point in time T3, the test position 50 at a point in time T4 and the test position 51 at a point in time T5. Exemplary values for T1-T5 can be 15 seconds, 20 seconds, 35 seconds, 55 seconds and 75 seconds. From the shown times T1-T5 the operator can conclude how long the acquisition of a sub-measurement region may last, inclusive of the table feed.

Figure 5:
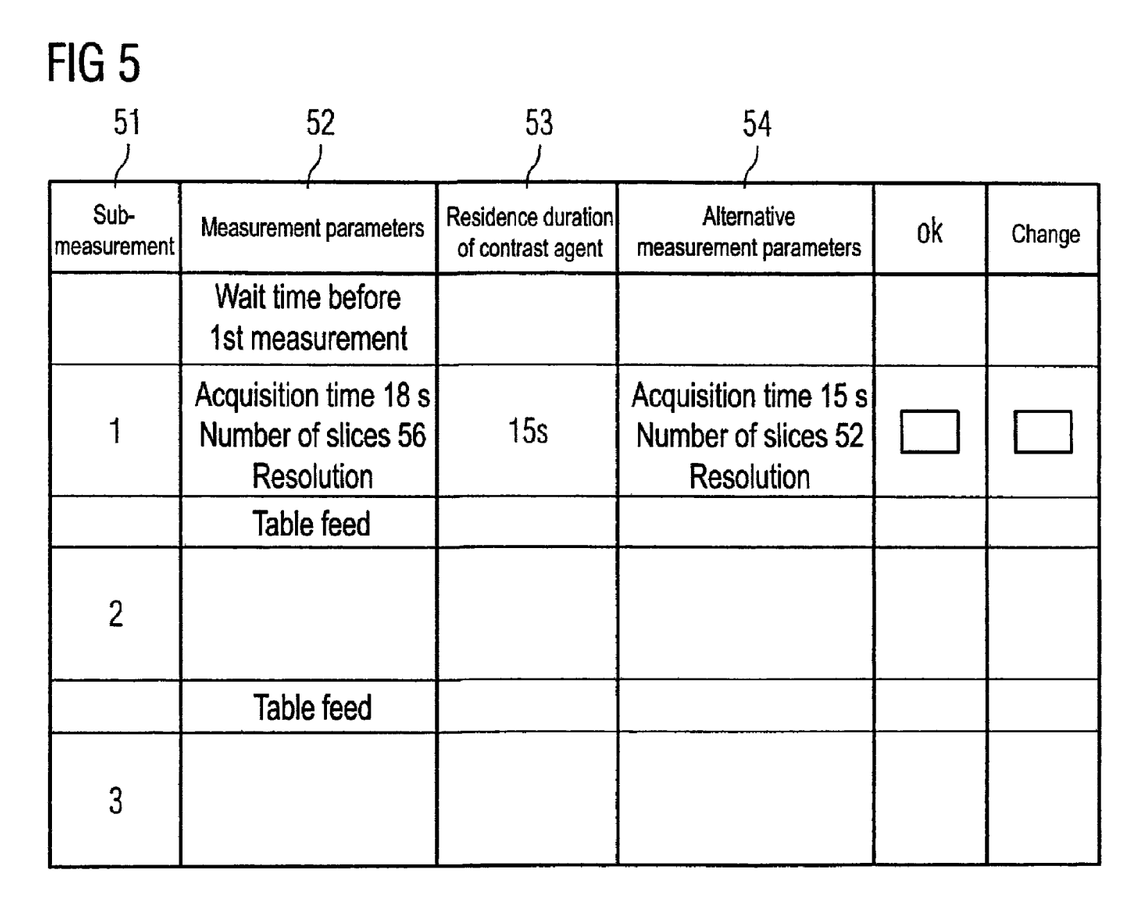
FIG. 5 is a table with the display of the automatically-determined workflow diagram for viewing by the operator.

An example of a measurement protocol that the system can generate after calculation of the transit time shown in FIG. 5. In the table presented in FIG. 5, the sub-measurements 1, 2, 3 (respectively separated by a table feed) are shown in a first column 51. Furthermore, before the first measurement the system waits so that the contrast agent injection and the measurement of the first sub-region can be started simultaneously. Furthermore, the proposed measurement parameters for the acquisition in the various sub-measurement regions (column 52) and the residence duration of the contrast agent in the various measurement regions (column 53) are shown in the table from FIG. 5. The user can either adopt or change the propose measurement parameters. Alternative measurement parameters that can be used as alternatives to the measurement parameters from column 52 are shown in column 54. When the transit time of the contrast agent is significantly faster and the individual measurements are no longer adapted such that good image quality is ensured, the user can suggest an application with two injections. Depending on the workflow (single or double injection), the measurements are first implemented before contrast agent administration. The user is subsequently prompted to apply the contrast agent and to simultaneously start the MR system. However, the system will only start the first sub-measurement when the contrast agent has reached this region. All following measurements ensue according to the determined workflow. In double injection measurements the sub-measurements that are acquired after the second injection are measured individually as prior and post contrast measurements after the progression of the first injection. When all measurements have occurred, the images are automatically subtracted and merged in a typical manner. With the inventive, method flawed exposures are avoided, the image quality is improved via optimally adapted parameters, the residence duration of the examination person in the magnet is shortened. Furthermore, the examination person can be spared the necessity of a further contrast agent injection when the acquisition does not succeed. Overall the acquisition technique is simplified, such that even less trained operators can implement the angiography measurements.

Although modifications and changes may be suggested by those skilled in the art, it is the intention of the inventors to embody within the patent warranted hereon all changes and modifications as reasonably and properly come within the scope of their contribution to the art.

We claim as our invention:
1. A method for planning an angiography image acquisition of a body region of a subject in a magnetic resonance system having a field of view, said body region being larger than said maximum field of view, said method comprising the steps of:
   establishing an upper boundary and a lower boundary of said body region, said upper boundary designating the abdomen of the subject and the lower boundary designating the lower legs of the subject, and making the respective designations of said upper boundary and said lower boundary accessible to a control unit of the magnetic resonance system;
   in said control unit, automatically dividing said body region into an initial division comprising a plurality of sub-measurement regions between the abdomen and the lower legs of the subject dependent on said upper boundary and said lower boundary, in which sub-measurements are to be conducted in succession to acquire diagnostic angiography image information from each of the sub-measurement regions by moving the subject through the magnetic resonance system to cause said sub-measurement regions to move successively into said field of view, said sub-measurement regions comprising a first sub-measurement region at the abdomen of the subject and a last sub-measurement region at the lower legs of the subject;
   prior to acquiring said diagnostic angiography image information, injecting a test bolus of a contrast agent into the subject and detecting arrival of the injected test bolus into only the respective first and last sub-measurement regions by acquiring magnetic resonance data only from the respective first and last sub-measurement regions by detecting when a magnetic resonance signal value reaches a threshold in vessels in the respective first and last sub-measurement regions;
   from the respective arrival times of the test bolus in the first and last sub-measurement regions, automatically determining, in said control unit, a detected transit time of the test bolus through the body region;
   in the control unit, automatically determining, a workflow for executing acquisition of said diagnostic angiography image information of an entirety of said body region, comprising a executing sequence of sub-measurements for receptively acquiring magnetic resonance data from all of the sub-measurement regions, and a time duration for acquiring said magnetic resonance data in all of the sub-measurements; and in said control unit, automatically comparing said time duration and said detected transit time to determine whether the initial division of the body region into said plurality of sub-measurement regions allows said workflow to be completed within said detected transit time and, if not, automatically adapting said sub-measurements and said sub-measurement regions to cause said workflow to have a time duration within the detected transit time.

2. A method as claimed in claim 1 comprising acquiring overview magnetic resonance data from the examination subject and generating overview images from the overview data, and establishing said upper boundary and said lower boundary of the body region from said overview images.

3. A method as claimed in claim 2 wherein said angiography image acquisition is a whole-body angiography image acquisition, and comprising automatically determining, in said control unit, said upper boundary and said lower boundary from said overview images.

4. A method as claimed in claim 2 wherein said angiography image acquisition is a partial-body angiography image acquisition, and comprising manually establishing at least one of said upper boundary and said lower boundary from said overview images.

5. A method as claimed in claim 1 comprising automatically determining said initial division in said control unit to comprise a plurality of said sub-measurement regions that overlap each other to cover an entirety of said body region, dependent on said upper boundary and said lower boundary.

6. A method as claimed in claim 1 comprising obtaining overview data of the entirety of the body region and generating overview images of the entirety of the body region from said overview data, and displaying the sub-measurement regions and a workflow diagram representing said workflow at a visual display overlaid on said overview images.

7. A method as claimed in claim 6 comprising allowing manual modification of respective positions of said sub-measurement regions and said workflow diagram based on said visual presentation.

8. A method as claimed in claim 6 comprising graphically presenting a time curve of respective arrivals of the test bolus in the measurement regions overlaid on said overview images in said visual presentation.

9. A method as claimed in claim 1 comprising moving said examination subject on a table, operated with a table feed, to successively bring said sub-measurement regions into said field of view of said magnetic resonance system and, in said control unit, automatically determining a maximum data acquisition duration for each sub-measurement region from said transit time and said table feed.

10. A method as claimed in claim 1 comprising, in said control unit, introducing a time offset before acquiring data from said first of said sub-measurement regions to allow said angiography image acquisition and injection of the contrast agent to be started simultaneously to cause the contrast agent to arrive in said first of said sub-measurement regions substantially simultaneously with beginning acquisition of magnetic resonance data from said first of said sub-measurement regions.

11. A magnetic resonance system for planning an angiography image acquisition of a body region of a subject, comprising:
a magnetic resonance scanner having a field of view, said scanner being configured to receive said subject therein and said body region being larger than said field of view;
a control unit that operates said scanner, said control unit having access to respective designations of an upper boundary and a lower boundary of said body region, said upper boundary designating the abdomen of the subject and the lower boundary designating the lower legs of the subject;
said control unit being configured to automatically divide said body region into an initial division comprising a plurality of sub-measurement regions between the abdomen and the lower legs of the subject dependent on said upper boundary and said lower boundary, in which sub-measurements are to be conducted in succession to acquire diagnostic angiography image information from the respective sub-measurement regions by moving the subject through the magnetic resonance system to cause said sub-measurement regions to move successively into said field of view, said sub-measurement regions comprising a first sub-measurement region at the abdomen of the subject and a last sub-measurement region at the lower legs of the subject;
a contrast agent administration system that, prior to acquiring said diagnostic angiography image information, injects a test bolus of a contrast agent into the subject, said control unit being configured to operate said scanner to detect arrival of the injected test bolus only into the respective first and last sub-measurement regions by acquiring magnetic resonance data only from the respective first and last sub-measurement regions by detecting when a magnetic resonance signal value reaches a threshold in vessels in the respective first and last sub-measurement regions;
said control unit, from the respective arrival times of the test bolus in the first and last sub-measurement regions, being configured to automatically determine, a detected transit time of the test bolus through the body region;
said control unit being configured to automatically determine a workflow for operating said scanner to execute acquisition of said diagnostic angiography information an entirety of said body region, comprising execution of a sequence of sub-measurements for receptively acquiring magnetic resonance data from all of the sub-measurement regions, and a time duration for acquiring said magnetic resonance data in all of the sub-measurements; and
said control unit being configured to automatically compare said time duration and said detected transit time to determine whether the initial division of the body region into said plurality of sub-measurement regions and, if not, to automatically adapt said sub-measurements and said sub-measurement regions to cause said workflow to have a time duration within said detected transit time.

12. A method as claimed in claim 1 comprising detecting when said magnetic resonance signal value reaches a threshold in said vessels in the respective first and last sub-measurement regions that indicates that said test bolus is present in both of said first and last sub-measurement regions during a same arterial phase of blood circulation in said body region of said subject.

13. A magnetic resonance system as claimed in claim 11 wherein said control unit is configured to detect when said magnetic resonance signal value reaches a threshold in said vessels in the respective first and last sub-measurement regions that indicates that said test bolus is present in both said first and last sub-measurement regions during a same arterial phase of said body region of said subject.

* * * * *